United States Patent [19]

Schramm et al.

[11] Patent Number: 5,394,740
[45] Date of Patent: Mar. 7, 1995

[54] CAPTIVE DROPLET INTERFACIAL TENSIOMETER AND METHODS OF USE THEREOF

[75] Inventors: Laurier L. Schramm; Samuel Schürch, both of Calgary, Canada

[73] Assignee: University Technologies International, Inc., Calgary, Canada

[21] Appl. No.: 939,517

[22] Filed: Sep. 4, 1992

[51] Int. Cl.[6] ............................................. G01N 13/02
[52] U.S. Cl. ................................................. 73/64.48
[58] Field of Search ............................. 73/64.48, 64.52

[56] References Cited

U.S. PATENT DOCUMENTS

| | | | |
|---|---|---|---|
| 4,953,389 | 9/1990 | Schurch | 73/64.4 |
| 4,988,377 | 1/1991 | Manalastas et al. | 71/28 |
| 5,031,449 | 7/1991 | Kuwana et al. | 73/61.10 R |

OTHER PUBLICATIONS

Egon Matjevié (Editor); *Surface and Colloid Science;* "Surface Tension. Part II. The Measurement of Surface Tension" by J. F. Paddy; (1969) vol. 1; pp. 101-149.

Laurier L. Schramm (Editor); *Emulsions, Fundamentals and Applications in the Petroleum Industry;* Chapter 7: "Emulsions in Enhanced Oil Recovery" by Kevin C. Taylor and Blaine F. Hawkins; American Chemical Society, Washington (1992) pp. 263-293.

B. Hawkins, K. Taylor and H. Nasr-El-Din; "Mechanisms of Surfactant and Polymer Enhanced Alkaline Flooding: Application to David Lloydminster and Wainwright Sparky Fields"; *Petroleum Society of CIM and AOSTRA;* CIM/AOSTRA 1991 Technical Conference in Banff, Apr. 21-24, 1991, pp. 28-1 through 28-16.

H. A. Nasr-El-Din and B. F. Hawkins; "Recovery of Waterflood Residual Oil Using Alkali, Surfactant and Polymer Slugs in Radial Cores"; *Revue de L'Institut Francais du Pétrole* (1991) vol. 46, pp. 199-219.

J. F. Boyce, S. Schurch, Y. Rotenberg and A. W. Neumann; "The Measurement of Surface and Interfacial Tension by the Axisymmetric Drop Technique"; *Colloids and Surfaces* (1984) vol. 9, pp. 307-317.

J. D. Malcolm and C. D. Elliott; "Interfacial Tension from Height and Diameter of a Single Sessile Drop or Captive Bubble"; *The Canadian Journal of Chemical Engineering* (Apr. 1980) vol. 58, pp. 151-153.

E. Lefebvre du Prey; "Méthode D'interprétation de la Goutte Posée Pour Mesurer la Tension Interfaciale et L'angle de Contact"; *Revue de L'institut Francais du Pétrole* (Mar. 1968) pp. 365-373.

*Primary Examiner*—Hezron E. Williams
*Assistant Examiner*—Michael Brock
*Attorney, Agent, or Firm*—Burns, Doane, Swecker & Mathis

[57] ABSTRACT

A method and an apparatus for determining the interfacial or surface tension, static or dynamic, between two liquids or between a gas and a liquid under conditions of varying temperature and pressure; and a method for adjusting the interfacial or surface tension in a petroleum reservoir for enhanced oil recovery. A tensiometer is provided which is capable of measuring interfacial or surface tension under pressure and temperature conditions which simulate those present in an actual petroleum reservoir. Measuring the interfacial and surface tension values under actual reservoir conditions then enables the selection of surfactants and other materials for adjusting the interfacial and surface tension to desired values for optimizing the enhanced oil recovery from that reservoir. A tensiometer is provided which includes a calibration body which is imaged along with the image of the test droplet in the tensiometer chamber. This imaging of both the calibration body and the test droplet provides the capability of correction of distortions in the image due to the nature of the chamber window for high pressure and/or high temperature measurements. The tensiometer is also provided with a surface against which the test droplet is imaged and measured, which is an annealed ionomer polymer coating on a polymer surface.

5 Claims, 3 Drawing Sheets

CAPTIVE DROPLET INTERFACIAL TENSIOMETER AND METHODS OF USE THEREOF

FIELD OF THE INVENTION

The present invention relates to a method and an apparatus for determining interfacial or surface tensions at the interface between two immiscible fluids: liquid/-liquid or gas/liquid. In particular the invention relates to a method and an apparatus suitable for determining very low interfacial tensions under temperature and pressure conditions simulating a petroleum reservoir.

BACKGROUND OF THE INVENTION

Although the region of contact between two immiscible phases may be very thin, the behavior at this transition area, or interface, is very important. For example, the determination of the interfacial tension of a system can be used as a means of determining necessary types and concentrations of solutions or additives to add to a petroleum-containing reservoir in order to lower the capillary forces preventing oil displacement and to enhance oil recovery from a secondary or tertiary oil recovery process. Common materials used to lower surface or interfacial tension are natural or synthetic surfactants.

The available methods of surface and interfacial tension measurements include the capillary rise, drop-weight and drop-volume, maximum bubble pressure, du Nouy ring, Wilhelmy plate, captive bubble, pendant drop, sessile drop and spinning drop methods. Comparisons of most of these methods are given by J. F. Padday in Surface and Colloid Science, E. Matijevic (Editor), Wiley-Interscience, New York, Vol. 1, p. 101, 1969 and by W. D. Harkins in Physical Methods of Organic Chemistry, A. Weissberger (Editor), Interscience, New York, 1959. These methods of surface tension determination are impractical or inoperative under conditions which approximate or simulate actual petroleum reservoir conditions. It is desired to have an instrument capable of conveniently measuring the following parameters of either interfacial (liquid/liquid) or surface (gas/liquid) tensions, under either dynamic (function of contact time) or static (fixed contact time), and under reservoir conditions of temperature and pressure whether the tension values may be high (80 mN/m), low (1 mN/m) or ultra-low ($10^{-4}$ mN/m). An apparatus capable of conveniently measuring the desired interfacial or surface tension values of various materials under reservoir conditions would be very useful in enabling the efficient selection of effective surfactants and other additives for use in a petroleum reservoir to enhance oil recovery therefrom.

In U.S. Pat. No. 4,953,389, to Schurch the substrate surface formed of an agar gel on an inert metal was adequate for maintaining the proper wetting condition under conditions employed therein. This was found not to be the case for measurements at elevated temperatures and furthermore not suitable for some kinds of interfacial tension measurements where chemical materials could diffuse into the gel structure.

Accordingly, it is an object of the present invention to provide a simple apparatus for determining interfacial or surface tensions at the interface between two immiscible fluids. More specifically, it is an object of the present invention to provide a means of determining the interfacial tension between two liquids at realistic petroleum reservoir conditions temperatures and pressures where the interfacial tension may be very low in magnitude.

SUMMARY OF THE INVENTION

In one aspect this invention provides a method of determining the interfacial or surface tension of the interface between two immiscible fluids comprising the steps of providing a first liquid medium in a chamber, injecting a small body of a second immiscible fluid, allowing said small body of the second fluid to come to rest against a substrate surface of the chamber, which surface comprises an annealed ionomer coating, and determining the interfacial or surface tension between the first and second fluid from the shape of said small body of the second fluid.

In another aspect this invention provides a method of selecting materials for use in a petroleum reservoir for enhanced oil recovery therefrom comprising the steps of providing an aqueous liquid medium in a chamber, injecting a sample of the desired oil from the desired petroleum reservoir, allowing said oil sample to come to rest against a substrate surface of the chamber, adjusting the chamber conditions of pressure and temperature to simulate the oil reservoir condition, determining the interfacial or surface tension between the aqueous liquid and the oil sample, and selecting one or more materials which, when added to the aqueous medium, adjusts the interfacial or surface tension to a desired value.

A further aspect of the above methods includes selecting a surfactant to modify the interfacial or surface tension as desired under the petroleum reservoir simulated conditions to provide enhanced recovery of oil from the reservoir.

In another aspect this invention provides a captive sample tensiometer comprising a chamber for containing a liquid medium in said chamber, means for forming a sample body in said medium thereby forming an interface between the sample body and said liquid medium, surface means adapted for the sample body to rest against while in said liquid medium wherein the surface comprises an annealed ionomer coating on a polymer substrate, and means for determining the surface tension of the sample body from the shape of the sample body.

In another aspect this invention provides a captive sample tensiometer comprising a chamber for containing a liquid medium in said chamber, means for forming a sample body in said medium thereby forming an interface between the sample body and said liquid medium, surface means adapted for the sample body to rest against while in said liquid medium wherein the surface comprises an annealed ionomer coating on a polymer substrate, and calibration means comprising a solid spherical body adapted to be positioned in the chamber in the same vertical plane as the sample body resting against the surface; and means for determining the surface tension of the sample body from an image of the shape of the sample body and for correcting for any distortion in said image by comparing said image to an image of the calibration body. The surface means can be hydrophilic or hydrophobic depending on the nature of the sample body and the liquid medium.

In another aspect this invention provides a method of preparing a surface suitable for wetting with a fluid comprising the steps of providing a polymer surface, coating the surface with a solution of an ionomer in an organic solvent, heating the coated surface at a temperature and time sufficient to anneal the ionomer on said surface thereby forming a coating of a thin layer of the ionomer bonded onto the polymer surface.

DETAILED DESCRIPTION OF THE INVENTION

Figure 1:
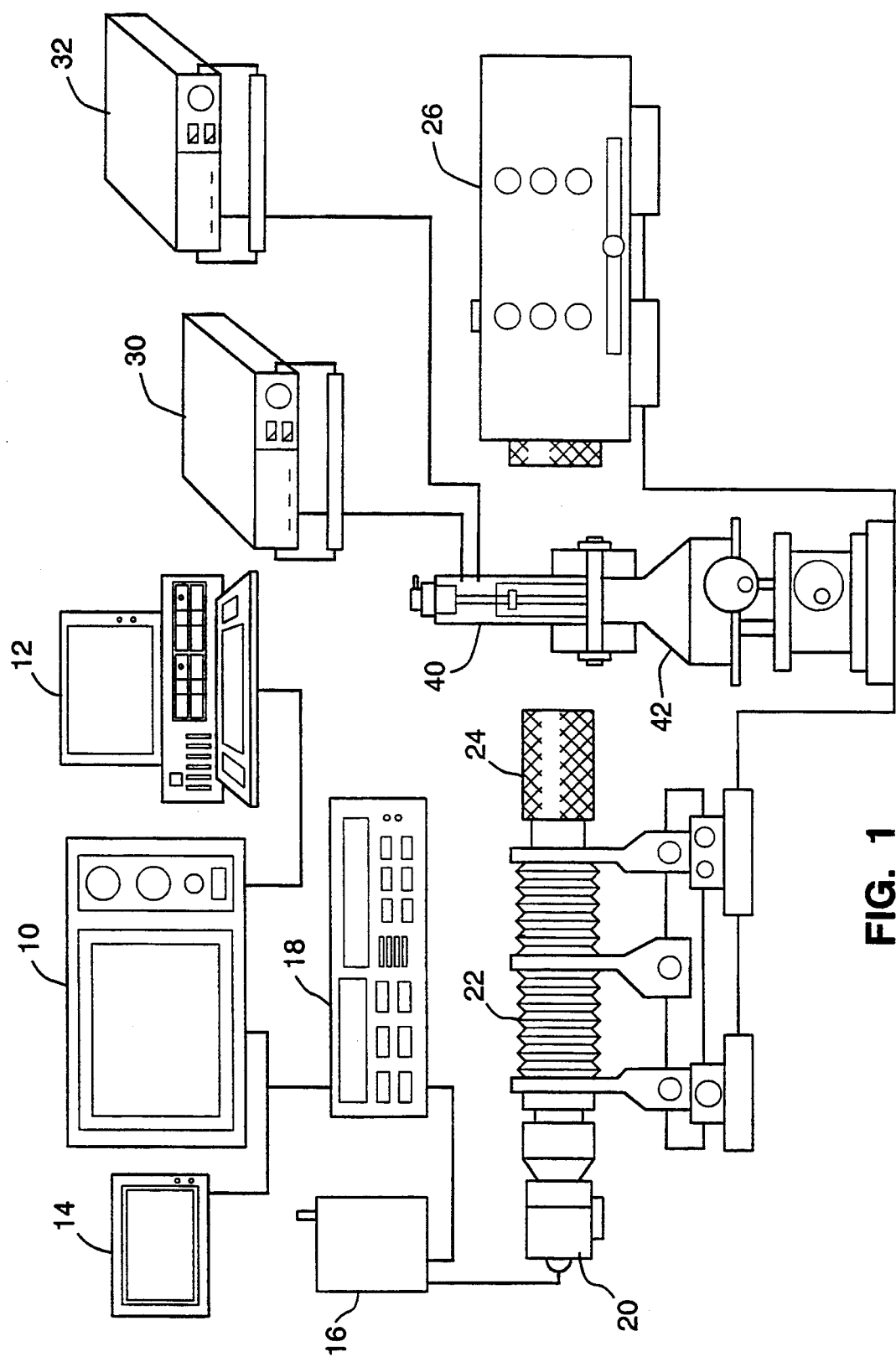
FIG. 1 shows a schematic illustration of the system employing the captive drop apparatus of this application invention.

As indicated above in the background of the invention, applicants have determined that it is desirable to be able to utilize a tensiometer to measure the interfacial or surface tension between certain fluids, in particular between oil in a petroleum reservoir and an aqueous medium used for enhanced oil recovery in that reservoir. Applicants have also determined that it is preferable to be able to measure those properties under temperature and pressure conditions which simulate those present in the petroleum reservoir itself. Upon finding that prior art tensiometers and methods were either inadequate or inoperable under such desired conditions of temperature and pressure, applicants herein have developed several aspects of the tensiometer art to enable convenient measurement of the desired properties and values under desired conditions. The tensiometer apparatus and measurement methods according to this invention provide convenient and reliable measurement of interfacial and surface tension properties, thereby enabling selection of surfactants, additives or other materials which are useful in increasing the efficiency and effectiveness of the enhanced oil recovery from petroleum reservoirs.

It is important to have accurate measurements of the interfacial or surface tension of a sample from a petroleum reservoir, particularly under the actual conditions which exist in the reservoir. Once the interfacial or surface tension values are accurately determined, then various materials and additives can be formulated for an aqueous phase injection into the petroleum reservoir for effective enhanced oil recovery. According to the present invention, the interfacial and surface tension can be determined from measurements in the tensiometer under conditions which simulate the actual conditions that exist in the reservoir, materials and additives can be selected for adjustment of the interfacial and surface tension properties, then those materials can be added to the aqueous phase and the system again tested in the tensiometer under reservoir conditions to determine if the desired adjustment of the interfacial and surface tension properties has been achieved. It will be apparent to one skilled in the art that once the interfacial and surface tension properties can be accurately measured according to the present invention, then it is well recognized in the art how to select various surfactants, alkalis, polymers or other materials or additives for adjusting the interfacial and surface tension properties to effect the desired enhanced oil recovery. For example, see *Emulsions, Fundamentals and Applications in the Petroleum Industry*, (Laurier L. Schramm, Editor), Ch. 7: "Emulsions in Enhanced Oil Recovery" by Kevin C. Taylor and Blaine F. Hawkins, pp. 263–293, American Chemical Society, Washington (1992); B. Hawkins, K. Taylor and H. Nasr-El-Din, "Mechanisms of Surfactant and Polymer Enhanced Alkaline Flooding; Application to David Lloydminster and Wainwright Sparky Fields," *Proceedings of the CIM/AOSTRA*, 1991 Technical Conference in Banff, Alberta, Apr. 21–24, 1991, CIM/AOSTRA Paper Number 91-28; and H. A. Nasr-El-Din and B. F. Hawkins "Recovery of Waterflood Residual Oil Using Alkali, Surfactant and Polymer Slugs in Radial Cores," *Revue de L'Institut Francais du Pétrole*, Vol. 46, pp. 199–219, (1991).

As disclosed and explained herein, one of the problems encountered in measuring the interfacial and surface tension properties under pressure and temperature conditions which simulate the high pressure and sometimes high temperature conditions present in an actual petroleum reservoir, therefore, the chamber in the tensiometer by necessity must be a high pressure chamber. In order to have visual access for imaging the test droplet in the chamber, the chamber by necessity is required to have thick glass or quartz windows for such visual access. Such a glass or quartz window must be of sufficient thickness to withstand pressure and temperature conditions which simulate conditions present in an actual petroleum reservoir. As a consequence, it was found that certain visual distortions of the image can occur which interfere with obtaining accurate and reliable image information from which to analyze the shape of the droplet and calculate the interfacial and surface tension values. As explained herein, one aspect of this invention involves the use of a visual reference standard within the chamber from which any distortions can be detected and corrections can be made for those distortions. The reference standard used according to this invention in the tensiometer chamber comprises a solid body of a known or standard shape, such as a disk or sphere, which will not change in shape or dimensions during the tests. This reference standard or calibration body is positioned in the same vertical access as the droplet under analysis. The image which is taken of the droplet under observation also simultaneously includes an image of the circular or spherical reference body. Alternatively, separate magnification images of the droplet and reference body may be taken sequentially, providing that they are taken under precisely the same conditions. That is, that between the taking of the two images no changes occur in the cell, the cell's contents, the camera, focussing system or illuminating system settings, or in the positioning along the optical path axis of any of the camera, focussing system, cell or illuminating system. Since it is known that the disk or sphere is perfectly round, then any distortions or alterations in the image can be corrected by using the reference body for calibration of the image. It will be apparent to one skilled in the art based on the disclosures herein that a reference body of any desired shape can be used and that once the image of the test droplet also includes or is supplemented by an image of the reference body under constant conditions, the calibrations and corrections for any distortions in the system can be made in a straight forward manner.

In one aspect, applicants herein have developed an improved captive droplet cell with respect to the surface against which the sample droplet of the immiscible liquid rests in order to measure its shape and properties to determine interfacial and surface tension values. As explained herein, it has been found that providing a particular surface, which is a polymer coated with an annealed ionomer, such as a polytetrafluoroethylene surface coated with a perfluorosulfonate ionomer, provides a surface in the captive droplet cell which is capable of withstanding the temperatures and pressures desired for simulating conditions present in petroleum reservoirs. It has been found that this surface is stable and reliably consistent under wide variations of temperature and pressure.

In another aspect, applicants have developed a captive droplet cell which contains a calibration body for direct comparison of the sample droplet to the calibration body. This calibration body aspect of the present invention has been found to be particularly useful in the embodiments of captive droplet cells known in the art but which have not contained a calibration means as well as in the embodiments of the novel captive droplet cells illustrated herein where video images of the sample droplet are employed to characterize and calculate the changes in shape of the droplet in response to various conditions and/or additives in the captive droplet cell. According to this invention, the calibration body being present in the cell provides a direct and convenient comparison and reference criteria, particularly for video imaging and computerized analysis of the shape of the sample droplet.

As a result of the above developments, the invention in this application also involves the method of preparing the surface in the captive droplet cell for contacting the sample droplet. The invention also involves the method of measuring interfacial or surface tension employing that surface employing particular configurations of the captive droplet cell as described above.

The method of this invention involves placing a droplet of liquid or a bubble of gas into a chamber filled with another immiscible liquid. Although in principle either phase may be used to form the captive droplet, it is frequently advantageous to use the less dense phase to form the captive droplet and the more dense phase to form the bulk or external phase. When the droplet or bubble rises to the top of the cell, it will contact a solid support surface. The surface must be completely wetted by the bulk phase if very low interfacial tension values are to be determined. The deformation of the captive droplet due to the balance of interfacial tension and gravity forces will give a characteristic droplet shape such that an image thereof may be captured and analyzed to calculate interfacial or surface tension.

Determination of the interfacial tension frown the dimensions of a drop image requires a minimum of the position of its apex, height at the apex and maximum diameter. To determine these variables, a computer generated image of the drop silhouette is used to determine its shape. Once the shape is defined, there are several methods that may be used to calculate the interfacial or surface tension from that shape, as discussed by S. Hartland and R. W. Hartley in *Axisymmetric Fluid-Liquid Interfaces*, Elsevier, N.Y., 1976. One method of determining interfacial tension involves the axis symmetric drop technique described by Rotenberg et at. in "The Measurement of Surface and Interfacial Tension by the Axisymmetric Drop Technique," *Colloids and Surfaces*, Vol. 9, pp. 307–317, 1984. This method involves fitting the shape of the droplet to a theoretical Laplacian function followed by analysis of that function for its parameters (i.e., the drop height, maximum diameter, drop volume, etc.). These parameters are then used together with the difference in densities to calculate the surface or interfacial tension.

A second method of interfacial tension determination is a method described by J. D. Malcolm and C. D. Elliott in "Interfacial Tension from Height and Diameter of a Single Sessile Drop or Captive Bubble" in *The Canadian Journal of Chemical Engineering*, Vol. 58, pp. 151–153, April 1980. This method requires that the contact angle be zero degrees and that a thin layer of molecules separates the contact surface from the drop. If these stipulations are met, the only dimensions required are the droplet equatorial diameter and the droplet height from apex to solid support surface. Once these values are found and the difference in densities are known, a calculation can be conducted to determine the interfacial or surface tension.

A third method of interfacial tension determination is described by E. Lefebvre du Prey in "Méthode D'interprétation de la Goutte Posée Pour Mesurer la Tension Interfaciale et L'angle de Contact" in *Revue de L'institut Francais du Pétrole*. pp. 365–373, March 1968. This method requires the equatorial diameter, the drop height, and the drop/support contact diameter. These measurements, together with the difference in densities, are used to calculate the interfacial or surface tension.

The first and third methods above can be used for determining interfacial or surface tensions where the interfacial or surface tensions are greater than about 1 mN/m. The second method may be used for determining interfacial or surface tensions lower than about 1 mN/m, providing that the contact angle/wetting condition requirements are met.

An illustration of one embodiment of the system of this invention is provided in FIG. 1. The first video monitor 10 and computer 12 are used for the droplet shape analysis while the second video monitor 14 is used for focusing the imaging camera 16. The video recorder 18 is utilized when dynamic systems are under observation or when analysis of the captive droplet system in question is not to be immediately performed. The recorder can also be used to provide previous images for further processing or for comparison to other images. The instruments employed to capture the images include a high-resolution video camera 20 fitted to a bellows 22 and a lens 24. The droplet in the cell is illuminated with an illuminator 26 aligned with the optical axis of the camera lens 24. Gauges 30 and 32 for the measurement of the cell temperature and pressure are also provided. The captive droplet cell 40 of the system is mounted on an adjustable positioning stand 42.

Figure 2:
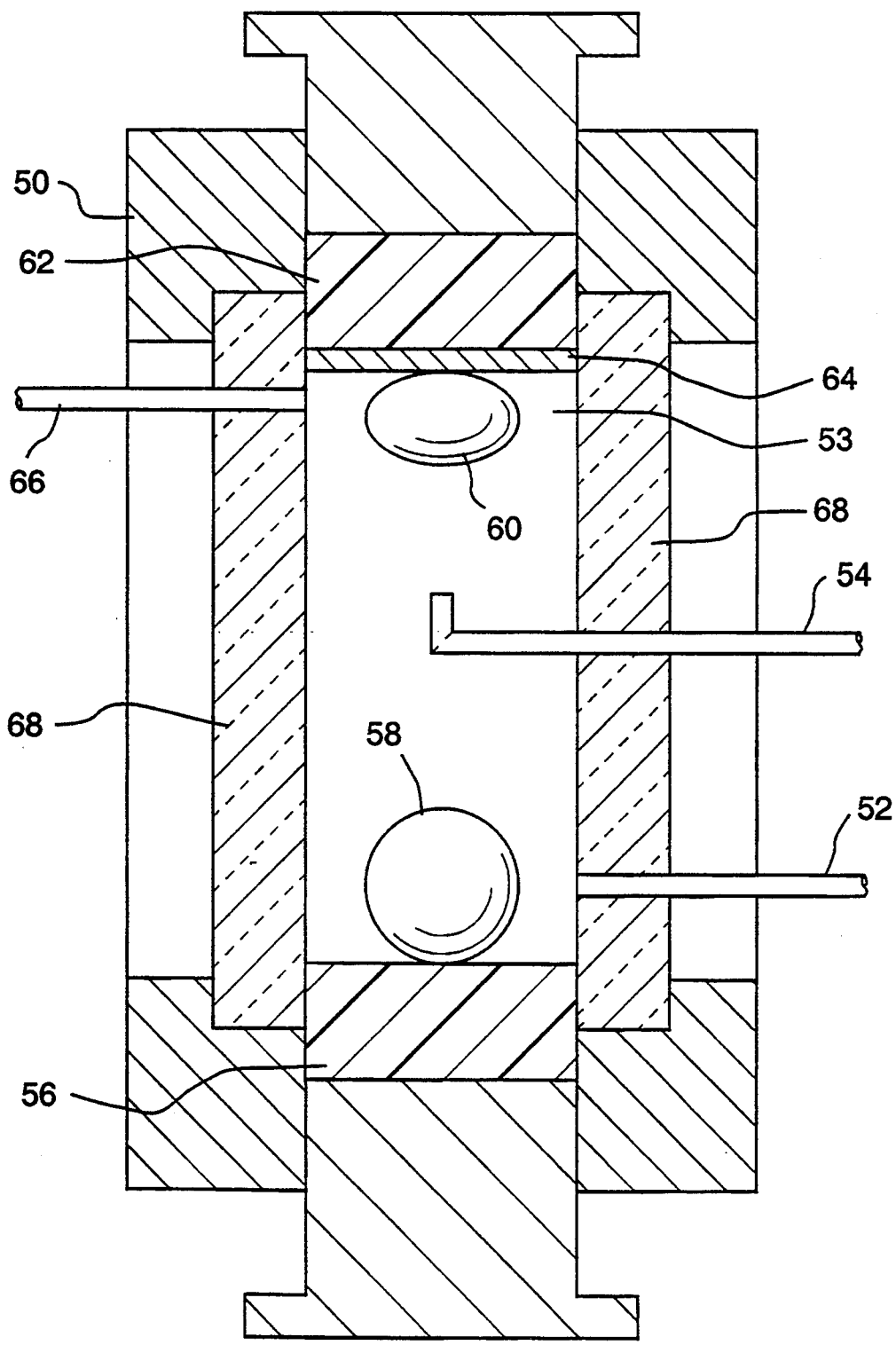
FIG. 2 illustrates an example of the captive drop cell according to this invention.

An embodiment of the captive droplet cell is illustrated in FIG. 2. The entire chamber or pressure vessel 50 must be capable of containing the desired pressures and withstand the desired temperatures and must remain leak proof. Provision is made for the separate injection of the external phase at inlet 52 and the second phase that will form the droplet or bubble at inlet 54. The chamber contains a support 56 on which is a calibration standard 58. The calibration body 58 must be centered in the same vertical plane as the center of the captive droplet or bubble 60 so that the droplet image may be magnified to the maximum extent possible while still being able to accurately determine the exact magnification used. We have found that a precision ruby sphere is convenient to use as the calibration standard 58. The droplet support substrate surface 62 is preferentially chemically inert, thermally stable and completely wetted by the external fluid phase 53 over the range of temperatures, pressures and chemical compositions with which it will come into contact. We have found that droplet support surfaces or contact surfaces constructed of "TEFLON", (DuPont trademark for polytetrafluoroethylene) are suitable and are preferred when the contacting surface 62 includes a surface treatment or a surface membrane 64 prepared from a "NAFION 601" (DuPont trademark for perfluorosulfonate ionomer) annealed on the polytetrafluorethylene surface. Outlet 66 is provided for removing the droplet and the external phase when desired. Glass windows 68 are provided to give visual access to the interior of the chamber.

In order for the chamber of FIG. 2 to withstand high temperature and pressure conditions the glass windows which give visual access to the droplet inside the chamber must necessarily be of appropriate thickness to withstand those conditions. Consequently, the glass windows and other aspects tend to induce certain distortions in the image of the droplet which is captured by the video camera for processing in the imaging system of this invention. Since precise and accurate images are needed in order to accurately determine the interfacial or surface tensions according to this invention, calibration body 58 is provided to serve as a standard reference image. Thus, any distortions induced by the glass windows or by the liquid phase in which the sample droplet and the calibration body are immersed can be corrected for the sample droplet by reference to the calibration body. Thus, the apparatus of this invention provides an apparent means for correcting any distortions in the sample droplet. Since it is known that the calibration body 58 is a true sphere, the computer imaging system can constantly monitor the image taken by the video camera of the calibration body 58. At any time and to any extent that the computer imaging system indicates that the calibration body 58 is not a true sphere or circle in the image, a correction can be computed and applied to the image of the sample droplet in order to reflect for the computer imaging system the true and actual shape of the sample droplet and the test chamber. Thus, it is important in carrying out the present invention that the video camera and imaging system either simultaneously capture the image of the sample droplet 60 along with the image of the calibration body 58 or that the system capture under precisely the same conditions the image of the sample droplet 60 and the image of the calibration body 58. This will better assure appropriate corrections to the extent they are indicated as needed by the deviations in the image of the calibration body.

We have discovered that under the conditions of high temperature and pressure, the requirements of being chemically inert, not being absorbent for component diffusion, and still providing a surface that would be completely wetted by an aqueous phase can be met by casting and annealing an ion polymer on a polymeric support to form thereon a surface treatment or membrane that, when cured, is insoluble in all solvents at room temperature and soluble in only a very few solvents at higher temperatures. The polymer support and the ion polymer coating can be any combination of materials that will meet the temperature, pressure and other requirements in the test chamber. The polymer support can be polyethylene, high density polyethylene, polypropylene, polytetrafluoroethylene and the like. The ion polymer coating on the support can be made from the acid or salt forms of ionomers of perfluorocarboxylic acid, perfluorosulfonic acid and the like. Certain difficulties were initially experienced due to formation of cast ionomer coatings or membranes, because such coatings were brittle and difficult to adequately anneal to the polytetrafluoroethylene. We have discovered that a procedure of coating a thin layer of the ionomer onto the polytetrafluoroethylene surface from a propanol solution in which the ionomer was dissolved and subsequently heating the coated surface 200° C. for two hours provided a coating with the desired polymer membrane physical properties. The ionomer coating or membrane must be carefully cast so as to coat the polytetrafluoroethylene in an even fashion. The droplet support or contact surface may either be flat or slightly concave upward so as to keep the droplet or bubble centered in the cell. Once the surface is coated and annealed, it must be properly cleaned by any good procedure. One such procedure involves cleaning with a sequence of hot nitric acid, boiling water, then aqueous potassium hydroxide solutions.

With the apparatus assembled and the phases in place in the cell, an image of the droplet is grabbed from the video camera image and transmitted to the computer and monitor. Once this is done the image has an intensity value for each picture element making up the screen. The image received may not exhibit perfect contrast between the droplet and the background illumination and may require adjusting to remove a bright spot that may appear in the center of the droplet. The object is to be able to clearly define the cross-sectional image of the droplet and the features of the shape of the droplet. These characteristics of the image may be improved by known image analysis techniques. The image is then scanned to determine the captive droplet or bubble shape. The scanning process may be conducted by taking vertical and horizontal lines across the image and saving the intensity of each picture element on each line at their respective coordinates. Once sufficient data scanning is accomplished, the data may be analyzed to fit a mathematical function such as an ellipse function. This may be done by a non-linear (Guassian) fitting method. Once the data is fitted, the appropriate shape parameters are then used to calculate the interfacial or surface tension from using a method, such as that of Malcolm and Elliott described earlier.

We have found that the axis symmetric technique for the surface tension determination is sufficiently accurate as long as the interfacial or surface tension to be determined is greater than about 1 mN/m. We have found that the method of Malcolm and Elliott for the surface tension determination is sufficiently accurate where the interfacial or surface tension to be determined is lower than about 1 mN/m. The method and apparatus described in the present invention may used for any of the good interfacial tension methods that rely on a calculation based on droplet shape or dimensions.

EXAMPLE 1

The surface tensions of several liquids were determined by placing an air drop in the cell containing the liquid of interest and then analyzing the shape of the air bubble. The cell used was built from a commercially available liquid level gage, a Jerguson Model T-20 from Jerguson Gage and Valve Co., Buffington, Mass. This liquid level gage was adapted by drilling new pans for the top and bottom plugs, for placement of the modified surface and for the other fittings, such as temperature and pressure sensors, to provide a cell as illustrated in FIGS. 1 and 2.

The values received for the surface tensions of pure liquids against an air bubble in contact with a substrate surface, that was completely wetted by the external liquid phase, are given in Table 1. The camera apparatus was always set to maximize the magnification of the drop while still being able to view the entire ball beating allowing minimization of calculation errors. The surface tensions measured were all within ±5% of the accepted values.

TABLE 1

Surface Tensions for Different Liquids and Solutions

| Fluid | Temperature (°C.) | Density Difference (g/cm$^3$) | Surface Tension | | |
|---|---|---|---|---|---|
| | | | Literature | Axis Symmetric (mN/m) | Malcolm & Elliot |
| Water | 24.1 | 0.996 | 72.11 | 70.43 | — |
| | 24.6 | 0.996 | 76.03 | 70.54 | 72.76 |
| Methanol | 21.3 | 0.789 | 22.50 | 22.16 | 21.86 |
| | 21.8 | 0.789 | 22.46 | 21.20 | 21.84 |
| | 22.3 | 0.788 | 22.42 | 22.49 | — |
| | 23.9 | 0.787 | 22.29 | 21.55 | — |
| Ethylene Glycol | 24.3 | 1.111 | 48.19 | 49.56 | — |
| | 24.6 | 1.111 | 48.2 | 47.2 | — |
| | 24.7 | 1.112 | 48.24 | 49.15 | — |
| 25.92% Aq NaCl | 23.8 | 1.195 | 82.63 | 83.39 | — |
| | 26.4 | 1.194 | 82.68 | — | 81.57 |

EXAMPLE 2

Four different systems were tested in the same apparatus as Example 1 for their interfacial tensions, shown in Table 2. The axis symmetric and Lefebvre du Prey methods for interfacial tension measurements failed to yield accurate values for these systems because the drop shape became too "flat". By maintaining a completely water wetted substrate contact surface it was possible to accurately use the Malcolm and Elliott method. In Table 2, "crude oil" refers to a sample of primary production crude oil obtained from the Lloydminster sand, in the David field, Alberta, Canada, used here as an example.

TABLE 2

| | | | Interfacial Tensions for Liquid-Liquid Systems. | | | |
|---|---|---|---|---|---|---|
| Bulk Liquid/Droplet Liquid | Temp. (°C.) | Density Difference (g/cm) | Surface Tension | | | |
| | | | Literature | Axis Symmetric | Malcolm & Elliot | Spin Drop |
| Water/ Octane | 23.1 | 0.297 | 50.3 | 49.3 | — | — |
| | 23.9 | 0.297 | 50.2 | 50.9 | — | — |
| Water/ Cyclohexanol | 23.0 | 0.050 | 3.92+ | 3.92 | 3.89 | — |
| | 23.4 | 0.051 | 3.92+ | 3.59 | 3.60 | — |
| 1% Na$_2$CO$_3$/ Crude Oil | 23.0 | 0.069 | — | — | 0.040 | 0.042 |
| 0.05% NaOH/ Crude Oil | 23.0 | 0.058 | — | — | 0.003-8* | 0.0038* |

+ at 16.2° C.
*minimum values

Figure 3:
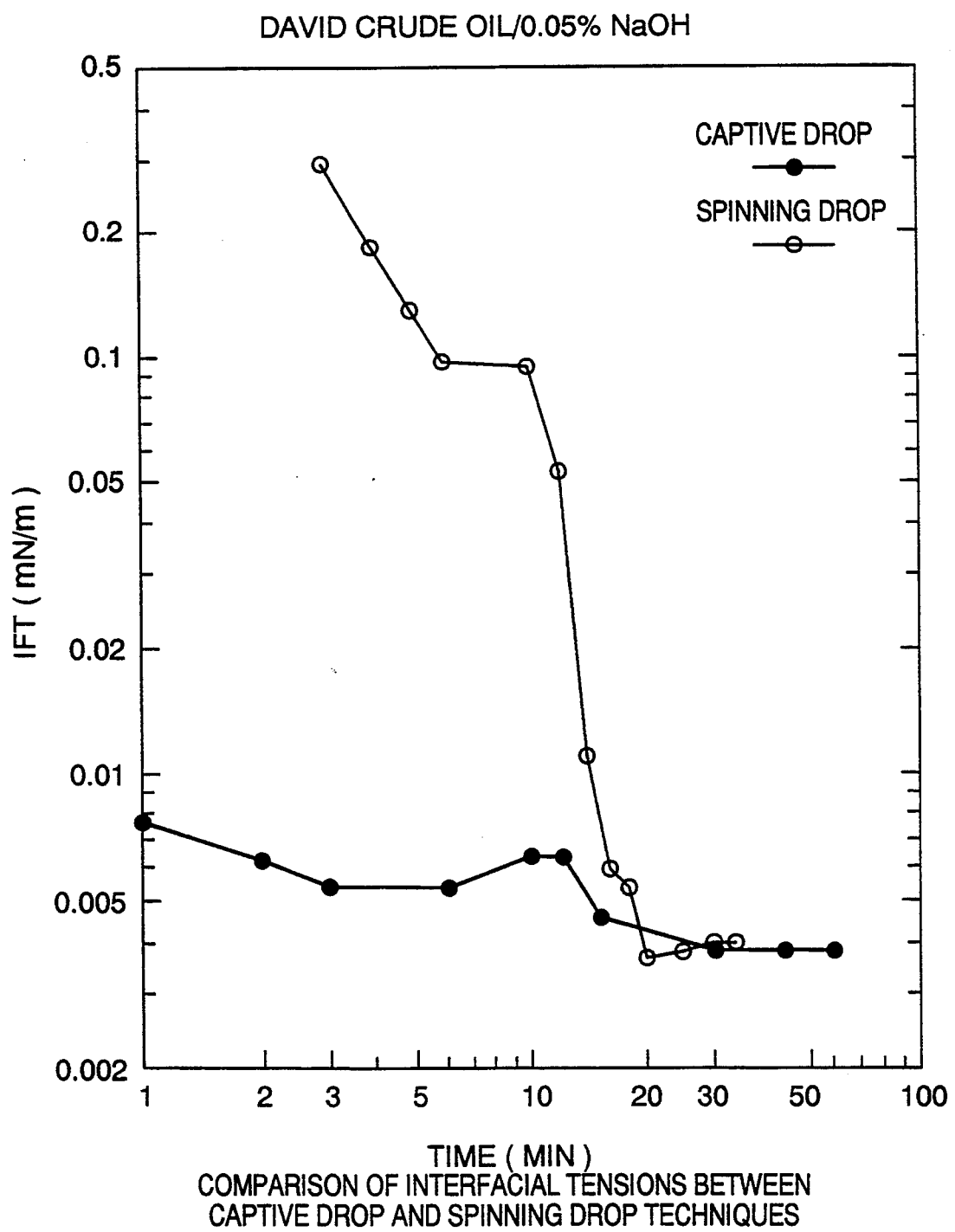
FIG. 3 is a graphic representation of a comparison of interfacial tensions obtained by the apparatus and method of this invention and by the spinning drop technique.

The David crude oil used here as an example also exhibits dynamic interfacial tension behavior in certain alkaline systems. A comparison of dynamic interfacial tensions measured for the system David crude oil and a 0.05% aqueous NAOH solution is shown in FIG. 3. Although not shown in this Figure, the interfacial tensions eventually increase with time, and after a period of some 12 hours, the interfacial tension values levelled off at about 2 mN/m. This kind of behavior is characteristic of many crude oil alkaline solution systems, in which interfacial tensions first decrease with time, reach a minimum value, and thereafter increase with time. Although all these features are of interest, the minimum interfacial tension value reached by a given system has been shown to correlate with achievable incremental oil recovery from a practical process by K. C. Taylor et at. in the Journal of Canadian Petroleum Technology, Vol. 29, pp. 50–55, 1990. FIG. 3 shows that the minimum values of interfacial tension measured by both the spinning drop technique and that of the present invention are in agreement. That the values of the interfacial tension measured by the spinning drop and captive droplet techniques were not identical for the entire experimental time period is thought to be due to differences in interfacial contact areas, mixing of bulk solution surrounding the oil drops, volume of the respective cells, and designation of the start time for each respective experiment.

The cell used in the above examples made from the Jerguson Model T-20 can be used for temperatures up to about 200° C. and pressures of up to about 2000 psi. Cells made from other commercially available sight gages, e.g., Jerguson Models T-30, T-40, etc. can employ higher temperatures and pressures, such as 5000 psi or more. It will be apparent to one skilled in the art how to match the cell construction to the conditions desired for use in the cell.

The various aspects of this invention have been described and exemplified by the above disclosure. The examples given herein are not to be considered limitations on the scope of this invention. The following claims set forth the scope of the invention herein.

What is claimed is:

1. A method of determining the interfacial or surface tension of the interface between two immiscible fluids comprising the steps of providing a first liquid medium in a chamber, injecting a body of a second immiscible fluid, allowing said body of the second fluid to come to rest against a substrate surface of the chamber, which surface comprises an annealed ionomer coating or a polymer substrate, and determining the interfacial or surface tension between the first and second fluid from the characteristics of the shape of said body of the second fluid in contact with said surface.

2. A method according to claim 1, wherein the annealed ionomer coating comprises a perfluorosulfonate ionomer coating.

3. A captive sample tensiometer comprising:
   a chamber for containing a liquid medium in said chamber; means for forming a sample body in said medium thereby forming
   an interface between the sample body and said liquid medium;

surface means in said chamber adapted for the sample body to rest against while in said liquid medium wherein the surface comprises an annealed ionomer coating on a polymer substrate;

means for adjusting the pressure and temperature conditions in said chamber;

means for adjusting and analyzing the shape of the sample body against said surface; and means for determining the interfacial or surface tension of the sample body from analysis of the observed shape of the sample body.

4. A tensiometer according to claim 3, wherein the surface means is hydrophilic.

5. A tensiometer according to claim 3, wherein the surface means is hydrophobic.

* * * * *